US00PP34473P2

(12) United States Plant Patent
Van Dijk

(10) Patent No.: US PP34,473 P2
(45) Date of Patent: Aug. 2, 2022

(54) ***ANTHURIUM* PLANT NAMED 'AN2169973'**

(50) Latin Name: ***Anthurium andraeanum* L.**
Varietal Denomination: 'AN2169973'

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,270

(22) Filed: Apr. 13, 2022

(51) Int. Cl.
*A01H 6/00* (2018.01)
*A01H 5/02* (2018.01)

(52) U.S. Cl.
USPC ..... Plt./365

(58) Field of Classification Search
USPC ..... Plt./365
See application file for complete search history.

*Primary Examiner* — Annette H Para
(74) *Attorney, Agent, or Firm* — Jondle & Associates, P.C.

(57) ABSTRACT

A new *Anthurium* cut flower plant named 'AN2169973' particularly distinguished by having strongly blistered and strongly glossy, white, oblong-cordate, and durable spathes that retain the original color for a very long period of time with shiny, dark green, and elliptical-cordate, durable leaves, white spadices with yellow-green tips, early and rich flowering continuously throughout the year, and a plant height of 60.0 cm to 70.0 cm is disclosed.

3 Drawing Sheets

Genus and species: *Anthurium andraeanum* L.
Variety denomination: 'AN2169973'.

BACKGROUND OF THE NEW PLANT

The present invention comprises a new and distinct variety of *Anthurium*, botanically known as *Anthurium andraeanum* L., and hereinafter referred to by the variety name 'AN2169973'. The new *Anthurium* plant is a product of a planned breeding program conducted by the inventor in Bleiswijk, the Netherlands. The objective of this breeding program was to create a new cut flower plant with a height of 60.0 cm to 70.0 cm having strongly blistered and strongly glossy, white, oblong-cordate, and durable spathes.

The new variety originated from a cross-pollination made in September 2007 in Bleiswijk, the Netherlands. The female parent was a white *Anthurium* pot plant designated '10639-01' (unpatented), and the male parent was a white *Anthurium* pot plant designated '10508-01' (unpatented).

A single plant was selected from the progeny of the stated cross in November 2010. Asexual reproduction of the new variety by tissue culture in 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 26, 2020 (Application no. 2020/2995), by Applicant who obtained the subject matter disclosed directly from the inventor. 'AN2169973' has not been made publicly available or sold anywhere in the world prior to the effective filing date of this application with the exception of sales or disclosures made one year or less before the effective filing date of this claimed invention by Applicant who obtained 'AN2169973' directly from the inventor.

SUMMARY OF THE INVENTION

The following are the most outstanding and distinguishing characteristics of this new variety when grown under normal horticultural practices in Bleiswijk, the Netherlands:

1) Strongly blistered and strongly glossy, white, oblong-cordate spathes;
2) White spadices with yellow-green tips;
3) Dark green, elliptical-cordate leaves; and
4) Relative position of spathe lobes is adpressed.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 60-week-old plant grown in a greenhouse in Bleiswijk, the Netherlands, in March 2022. Colors in the photographs may differ from the color values cited in the detailed botanical description, which accurately describe the actual colors of the new variety.

DESCRIPTION OF THE NEW VARIETY

Figure 1:
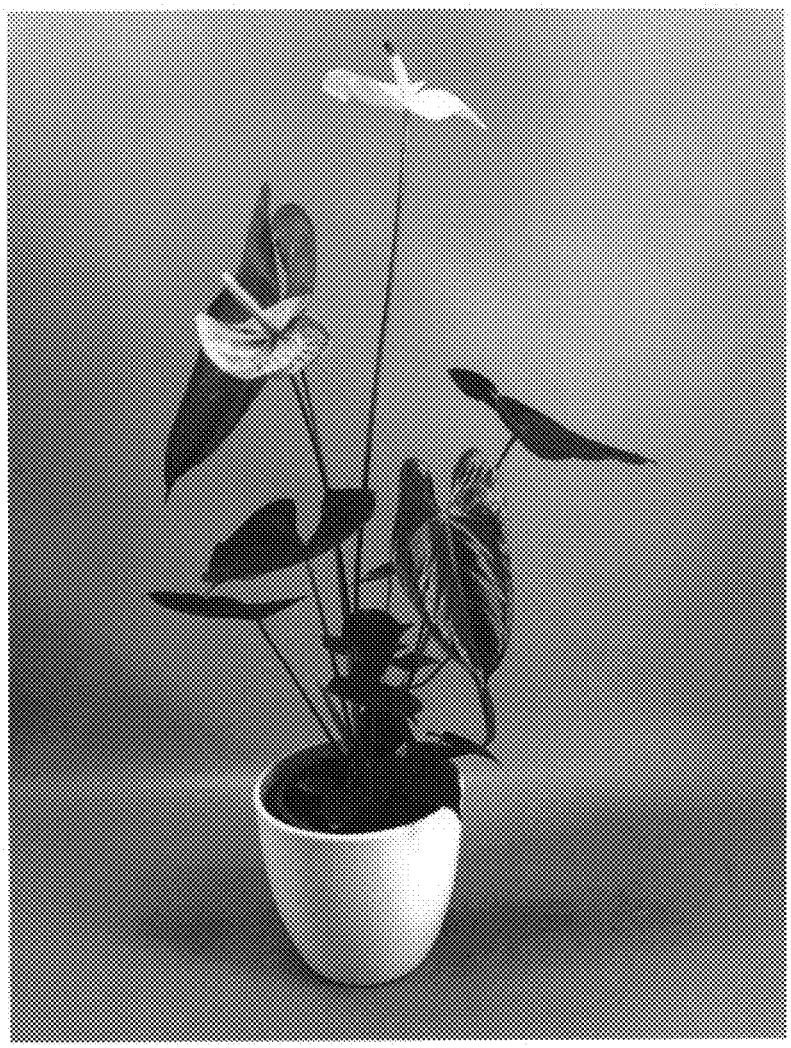
FIG. 1 shows the overall plant habit, including blooms and foliage.
Figure 2:
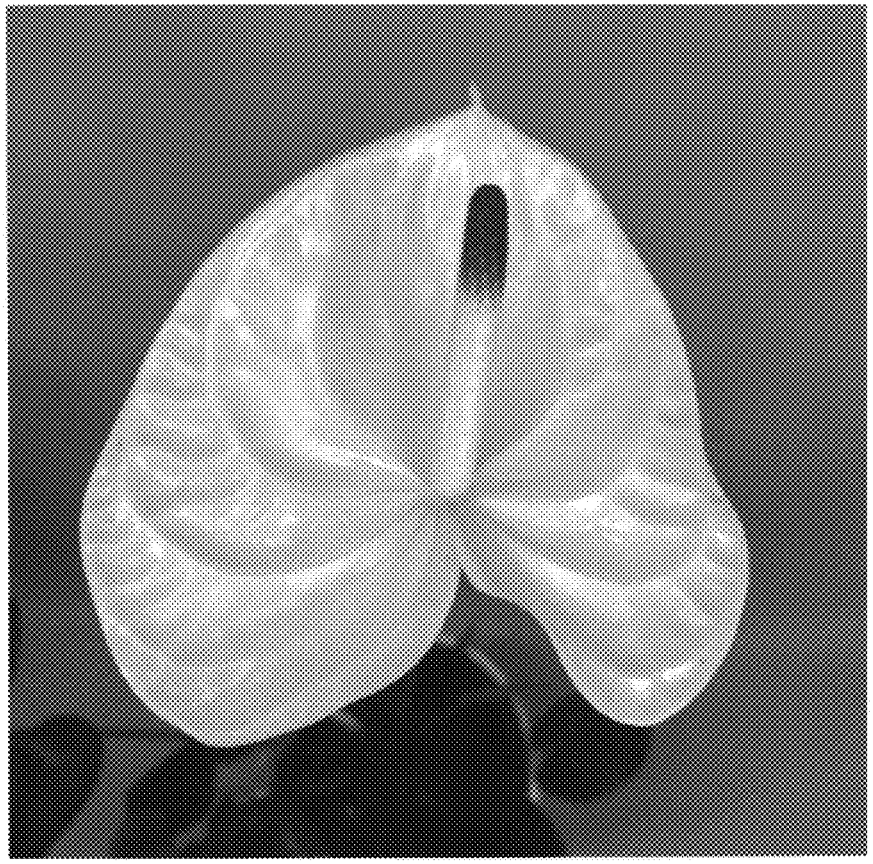
FIG. 2 shows a close-up of the mature spathe.
Figure 3:
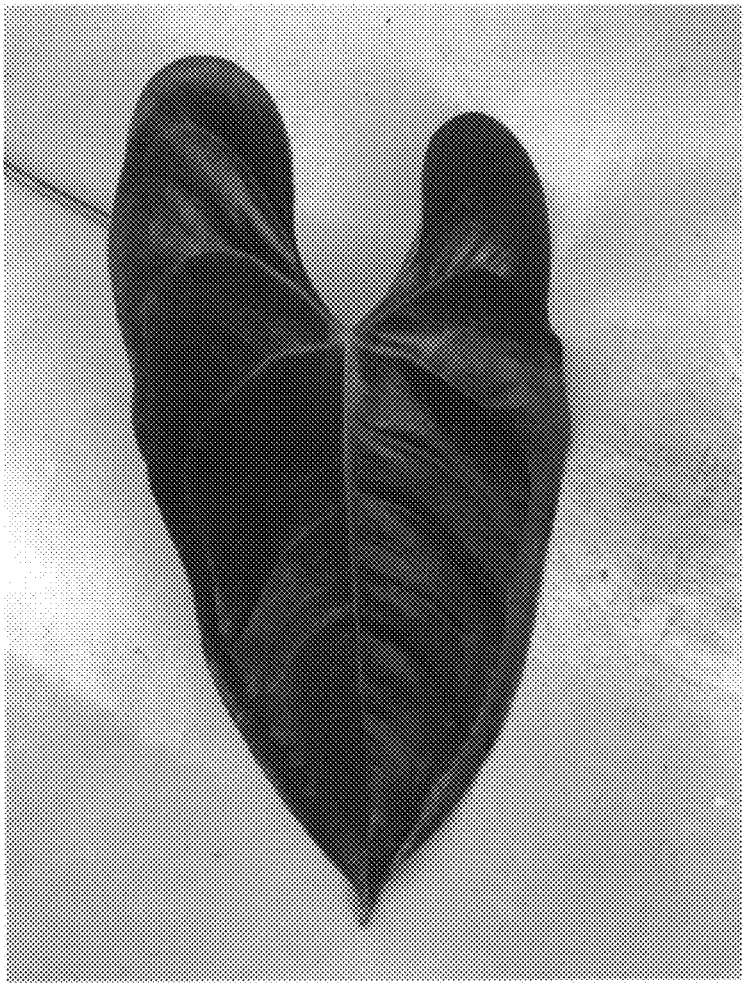
FIG. 3 shows a close-up of the upper leaf blade surface.

The following detailed description sets forth the distinctive characteristics of 'AN2169973'. The data which define these characteristics were collected from asexual reproductions carried out in Bleiswijk, the Netherlands. The plant history was taken on 60-week-old plants which were planted from tissue culture in 17-centimeter (diameter) pots and grown in a glass greenhouse between 19° C. and 24° C. Observations were made in March 2022. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'AN2169973'.

Parentage:

*Female parent*.—*Anthurium* plant '10639-01' (unpatented).

*Male parent*.—*Anthurium* plant '10508-01' (unpatented).

Plant:

*Propagation*.—Tissue culture.

*Root description*.—Fleshy-creamy (RHS 160D) colored roots with small hairy lateral roots having greenish-yellow (RHS 6A) colored root tips.

*Time to produce a finished flowering plant*.—55 to 66 weeks after planting in a 17-cm (diameter) pot.

*Growth habit*.—Upright.

*Height* (*measured from soil, including inflorescence*).—60.0 cm to 70.0 cm.

*Width* (*measured from leaf tips*).—47.0 cm to 52.0 cm.

Leaves:

*Immature leaves*.—Length: 21.0 cm to 23.0 cm. Width: 12.0 cm to 14.0 cm. Color: Upper surface: RHS 146B. Lower surface: RHS 146C. Texture (both upper and lower surfaces): Leathery, soft, thin, and glossy.

*Mature leaves*.—Length (fully expanded): 28.0 cm to 31.0 cm. Width: 14.0 cm to 16.0 cm. Shape: Elliptical cordate. Apex: Caudate. Base: Cordate. Leaf blade angle with the petiole: Between 110 degrees and 130 degrees. Leaf margin: Entire. Color: Upper surface: RHS 147A. Lower surface: RHS 146A. Texture: Upper surface: Leathery and thick. Lower surface: Glossy, leathery, and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS N144A.

*Lobes*.—Present. Arrangement: Leaf blade has two lobes extending past the petiole. The lobes are non-touching. Length of lobes of mature leaf blades: 7.0 cm to 9.0 cm. Width of lobes of mature leaf blades: 6.0 cm to 7.0 cm. Distance from petiole/leaf junction to highest point on lobes of mature leaf blades: 3.0 cm to 4.0 cm.

*Petiole*.—Cross-section: Round. Diameter: 0.4 cm to 0.5 cm. Length: 37.0 cm to 42.0 cm for a mature leaf size. Color: Mature leaf: RHS 144A. Immature leaf: RHS 144B. Cataphyll color surrounding the petiole: Outside: RHS 144C. Inside: RHS 145C.

*Geniculum*.—Length: 1.5 cm to 2.0 cm. Width: 0.5 cm to 0.6 cm. Color: RHS 144C.

Inflorescence:

*Arrangement*.—Single.

*Flowering habit* (*length of flowering season*).—Continuous.

*Number of inflorescences per plant*.—The plant produces 5 to 6 flowers in the period of one year.

*Fragrance*.—Absent.

*Longevity of inflorescence as a cut flower*.—30 days to 35 days.

Spathe:

*Buds*.—The spathe is tightly rolled around the spadix and extrudes from the peduncle sheath.

*Arrangement*.—Spathe angle with the peduncle is between 90 degrees and 110 degrees; the spathe stands on a wiry peduncle about 2.0 cm to 5.0 cm above the foliage.

*Shape*.—Oblong cordate.

*Apex*.—Abruptly acuminate.

*Base*.—Cordate.

*Texture*.—Strongly blistered and strongly glossy.

*Margin*.—Undulated.

*Size*.—Length: 12.0 cm to 13.0 cm. Width: 10.5 cm to 11.5 cm.

*Lobes*.—Present. Arrangement: The spathe has two lobes extending past the peduncle. The lobes are adpressed. Length: 4.0 cm to 5.0 cm. Width: 5.0 cm to 6.0 cm.

*Color*.—Just fully open: Upper surface: RHS NN155A. Lower surface: RHS NN155A. This white color remains for a very long period, at least more than 30 weeks after opening.

Peduncle:

*Shape*.—Erect.

*Cross-section*.—Round.

*Length*.—60.0 cm to 70.0 cm.

*Diameter*.—0.4 cm to 0.5 cm.

*Color*.—Yellow-green (RHS 144B) at the base; becomes reddish-orange (RHS 180B) toward the spathe.

Flowering time:

*General*.—One small, rooted, untreated tissue culture plant of 4.0 cm tall will flower for the first time, depending on the season, after 30 to 35 weeks.

Spadix:

*Size*.—Length: 5.0 cm to 6.0 cm (depending on flower size). Width (at apex): 0.6 cm to 0.7 cm. Width (at base): 0.7 cm to 0.8 cm.

*Shape*.—Columnar.

*Angle of spadix tip with peduncle*.—120 degrees to 140 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 144A. Mature: RHS 158C. Ages to: RHS 151A.

Flowers:

*Quantity per spadix*.—220 to 270.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 158C.

Reproductive organs:

*Stamens*.—Not visible.

*Pollen amount*.—Absent.

*Pistil*.—Quantity: 220 to 270. Length: Less than 0.01 cm. Color: RHS 158C.

*Style*.—Not observed to date.

*Stigma*.—Shape: Ovoid. Diameter: Less than 0.01 cm. Color: RHS 158C.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2169973' differs from the female parent plant '10639-01' (unpatented) in that 'AN2169973' has strongly blistered, oblong-cordate spathes, whereas '10639-01' has medium blistered, cordate spathes.

'AN2169973' differs from the male parent plant '10508-01' (unpatented) in that 'AN2169973' has oblong-cordate spathes with abruptly acuminate apexes, whereas '10508-01' has orbicular-cordate spathes with mucronate apexes.

'AN2169973' differs from similar commercial variety 'ANTHAQXM' (unpatented) in that 'AN2169973' has caudate leaf apexes, green cataphylls, and roots with no over color, whereas 'ANTHAQXM' has cuspidate leaf apexes, red cataphylls with green tips, and roots with light pink over color. Additionally, 'AN2169973' has shorter spadices than 'ANTHAQXM'.

'AN2169973' differs from similar variety 'ANTHAQUIRE' (unpatented) in that 'AN2169973' has caudate leaf apexes, green cataphylls, strongly blistered spathes, and roots with no over color, whereas 'ANTHAQUIRE' has acuminate leaf apexes, red cataphylls, medium blistered spathes, and roots with pink over color.

I claim:

1. A new and distinct variety of *Anthurium* plant named 'AN2169973', substantially as illustrated and described herein.

* * * * *